United States Patent [19]

Nelson

[11] Patent Number: 4,845,260
[45] Date of Patent: Jul. 4, 1989

[54] PREPARATION OF ALKYL SILANES

[75] Inventor: Gunner E. Nelson, Baton Rouge, La.

[73] Assignee: Ethyl Corporation, Richmond, Va.

[21] Appl. No.: 129,001

[22] Filed: Dec. 3, 1987

Related U.S. Application Data

[63] Continuation-in-part of Ser. No. 17,852, Feb. 24, 1987, Pat. No. 4,711,965.

[51] Int. Cl.$^4$ .................................................. C07F 7/08
[52] U.S. Cl. ..................................................... 556/478
[58] Field of Search ......................................... 556/478

[56] References Cited

U.S. PATENT DOCUMENTS

| | | | |
|---|---|---|---|
| 2,857,414 | 10/1958 | Schmidt | 556/478 X |
| 3,398,171 | 8/1968 | Giraitis et al. | 260/448.2 |
| 4,367,343 | 1/1983 | Tamborski et al. | 556/478 |
| 4,595,777 | 6/1986 | Bakshi et al. | 556/478 |
| 4,683,321 | 7/1987 | Nelson | 556/478 |
| 4,711,966 | 12/1987 | Nelson | 556/478 |

FOREIGN PATENT DOCUMENTS

| | | | |
|---|---|---|---|
| 825987 | 12/1959 | United Kingdom | 556/478 UX |
| 900132 | 7/1962 | United Kingdom | 556/478 UX |

OTHER PUBLICATIONS

Tamborski et al, *Ind. Eng. Chem. Prod. Res. Dev.* 22, 172–178 (1983), Synthesis & Prop. of Silahydrocarbons, A Class of Therm. Stable, Wide Liquid Range Fluids.
Ashby et al, *Inorg. Chem.* 2, No. 3, pp. 499–504 (1963).
Zakharkin et al, *Izvestiya Akademii Nauk SSSR, Seriya Khimicheskaya* No. 1, pp. 142–143 (Jan., 1966).
Gavrilenko et al, *Zhurnal Obshchei Khimii* 39, No. 5, pp. 1055–1058 (May, 1969).

*Primary Examiner*—Paul F. Shaver
*Attorney, Agent, or Firm*—John F. Sieberth; Philip M. Pippenger

[57] ABSTRACT

Silahydrocarbons having the formula RSiR'$_3$ are prepared by a three step process. In the first step in a preferred embodiment, sodium, aluminum, hydrogen and olefin (corresponding to the radical R') are reacted in the presence of a triorganoaluminum catalyst. In a second step, fresh catalyst is added and reaction continued. In a third step, the product of the second step is reacted with a trihaloalkylsilane to produce the RSiR'$_3$ product. Such products are useful as functional fluids.

10 Claims, No Drawings

PREPARATION OF ALKYL SILANES

CROSS-REFERENCE TO RELATED APPLICATIONS

Reference is made to two other applications filed in the name of Applicant, namely Application Ser. No. 17,852 filed Feb. 24, 1987, now U.S. Pat. No. 4,711,965, of which this application is a continuation-in-part, and Application Ser. No. 27,897 filed on Mar. 19, 1987, now U.S. Pat. No. 4,711,966.

FIELD OF THE INVENTION

This invention relates to preparation of alkali metal aluminum tetraalkyls (also known as alkali metal aluminates). This invention also relates to their use in the preparation of silahydrocarbons for use as functional fluids.

RELATED ART

Methods for the synthesis of tetraalkyl silanes include the reaction of alkyl magnesium halides or alkyl lithiums with halosilicon compounds; Tamborski et al, U.S. Pat. No. 4,367,343, and Tamborski et al, Synthesis and Properties of Silahydrocarbons, A Class of Thermally Stable, Wide Liquid Range Fluids, *Ind. Eng. Chem. Prod. Res. Dev.* 22, 172-178 (1983).

British patent No. 825,987 to Kali-Chemie AG discloses the reaction of trialkylaluminums with alkyl- or arylchlorosilanes.

Jenkner, British patent No. 900,132 (also to Kali-Chemie), pertains to the reaction of sodium aluminum tetraethyl with halosilanes, such as silicon tetrachloride, where the reactants are used in a ratio of 4 to 1.

Bakshi et al, U.S. Pat. No. 4,595,777, pertains to the process of reacting an alkylchlorosilane with a trialkylaluminum.

Ashby et al, *Inoro. Chem.* 2, No. 3, pp. 499-504 (1963) discusses formation of metal hydrides such as NaAlH4 and alkyl derivatives thereof.

Giraitis et al, U.S. Pat. No. 3,398,171, relates to the reaction of organosilanes and mixed metal compounds AMR$_n$ wherein A is an alkali metal and M can be aluminum. The process is conducted at a reaction temperature of −20° C. to +50° C.

Zakharkin et al, *Izvestiya Akademii Nauk SSSR, Seriya Khimicheskaya* No. 1, pp. 142-143 (January, 1966) discusses addition of NaAlH4 to olefins. Gavrilenko et al, *Zhurnal Obshchei Khimii* 39, No. 5, pp. 1055-1058 (May, 1969) discusses non-catalytic addition of sodium and alkyl substituted aluminum hydrides to alpha olefins.

SUMMARY OF THE INVENTION

This invention pertains to the preparation of tetraalkylsilanes, wherein one alkyl group is comparatively small and the other three are comparatively large. The small alkyl group has from one to about four carbon atoms, while the larger three groups have from about 8 to about 14 carbon atoms each. These products are prepared by a process which comprises reacting Na, Al, H$_2$ and olefin in the presence of an organoaluminum catalyst to prepare an intermediate product, which can be reacted with a trihaloalkylsilane to produce the desired product.

The process comprises three steps; they can be conducted in a single reactor without isolation of reaction intermediates. The tetraalkylsilane product can be used as a functional fluid.

DESCRIPTION OF PREFERRED EMBODIMENTS

In a highly preferred embodiment this invention comprises a process for the preparation of a tetraalkylsilane,

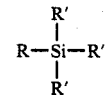

wherein R and R' represent alkyl radicals such that R has up to about 4 carbon atoms, and the radicals represented by R' are alike or different and have from about 8 to about 14 carbon atoms; said process comprising (a) reacting an alkali metal with aluminum, hydrogen and olefin in the presence of an organoaluminum catalyst, (b) adding additional catalyst to the reaction mixture to prepare an intermediate product, and (c) subsequently reacting the intermediate with a trihalosilane to produce the tetraalkylsilane.

For step (a), the preferred alkali metal is sodium. Its utility suggests the use of other alkali metals such as potassium or lithium. Aluminum is preferably employed in a slight excess over sodium. In general, it is used in amounts of from about 1.05 to 1.1 times its stoichiometric requirement. A greater or lesser amount of aluminum may be used if desired. The aluminum is preferably used in a powdered, or other reactive form. It may contain a promoter metal such as titanium.

The metals are reacted in the presence of hydrogen and olefin. Preferably, for each gram atom of sodium, at least about 2 moles of hydrogen is used, and at least about 4.0 moles of olefin are employed. The olefin is preferably used in excess, with the excess serving as liquid reaction medium. The amount of excess is not critical, and any convenient amount, e.g. from a 10 weight percent (or less) excess, to a 1000 weight percent (or greater) excess, can be used.

The olefin is preferably an alpha olefin. These react to form a straight chain alkyl group. Preferably the olefin has about 8 to about 14 carbon atoms, but olefins having more or less carbon atoms can be used. Preferably the olefin is solely composed of carbon and hydrogen, and more preferably it is readily available in commerce.

Most olefins available in large commercial quantities are made from natural products or by chain growth of ethylene. In either case, the olefin usually has an even number of carbon atoms. However, it is to be understood that an even number of carbon atoms is not critical, and olefins having an odd number of carbon atoms can also be used in this invention. Nevertheless, because of the more ready availability of even numbered olefins, the preferred olefin reactants for this invention have alkyl radicals (depicted by R' in the above formula) that are derived from one or more of the following olefins:

octene-1
decene-1
dodecene-1
tetradecene-1
hexadecene-1

The olefin need not be pure. Thus for example, a mixture of olefins such as hexene-1 and tetradecene-1, or octene-1 and decene-1 in a mole ratio of about 2 to 1 can be used. Optionally, the olefin may be mixed with an inert liquid reaction medium such as a paraffin; e.g. hexane or dodecane.

The process of step (a) is conducted in the presence of hydrogen pressure. A pressure within the range of 1500–2500 psig is preferred, but lower pressures and higher pressures can be used, if desired. The lower pressure limitation is determined by the rate of reaction; one uses enough $H_2$ pressure to afford a reasonable reaction rate. No real upper pressure limit is known. Hence, the upper extent of the pressure range is defined by equipment limitations, convenience, and similar considerations.

If desired, an operating pressure (e.g. 2000 psig) can be selected, and that pressure can be maintained by adding additional hydrogen during the course of the reaction, i.e. as the hydrogen becomes incorporated in the reaction product.

The reaction temperature is selected to give a reasonable rate of reaction; but is not so high as to cause a deleterious effect. Temperatures within the range of from about 140° C. to about 180° C. are preferred.

The reaction is catalyzed by an organoaluminum catalyst. Trialkylaluminums can be used. Preferably, the three organo groups in the triorganoaluminum are the same and rather small; i.e. they have from one to three carbons. Triethylaluminum is a preferred catalyst.

A catalytic amount of the catalyst is used. Preferably in step (a), an amount of catalyst equivalent to about 2 to about 10 mole percent (based on sodium) is employed. More preferably, about 5–7 mole percent of catalyst is used. One selects an amount of catalyst which catalyzes the desired reaction without catalyzing an untoward amount of olefin dimerization as a side reaction.

The reaction time is not a truly independent variable, but is dependent at least in part on the reactivity of the materials used in the process, and on the other reaction conditions selected. Generally, the process of step (a) is complete in less than about 10 hours.

For step (b), the product mixture of step (a) can be used in the same reaction vessel, and without workup. Thus, the reactor can be vented and the solid/liquid contents of the reaction vessel can be used as is. For step (b), additional catalyst is added and the resultant mixture reacted at a somewhat elevated temperature or temperatures.

The same amount of catalyst as described above can be used, i.e. an amount of from about 2 to about 10 mole percent based on the amount of sodium charged in step (a). As in step (a), one selects an amount of catalyst which gives a reasonable rate of reaction without an untoward amount of olefin dimerization.

For step (b), it is not necessary to use a triorganoaluminum catalyst (such as triethylaluminum) in which the organic radicals have one-three carbons. These materials can be used as catalysts if desired; however, it is preferred to use a triorganoaluminum in which the organic group(s) are the same as one or more groups that will appear in the product of step (c). Thus for example, tri-n-octylaluminum (TNOA) is a preferred catalyst for use with octene-1, or an olefin mixture containing same, i.e. when the product of step (c) has the formula $RSiR'_3$, and wherein at least one $R'$ radical is octyl.

If desired, additional olefin can be added for step (b) to make the reaction more fluid, and/or to insure that there is enough olefin for reaction. All catalyst and/or additional olefin can be added prior to beginning step (b). Alternatively, they can be added intermittently or continuously during the step.

The process temperature for step (b) is preferably above 130° C.; more preferably from about 160° C. to about 180° C. Somewhat higher and lower temperatures can be used. The process of step (b) is generally complete in five hours or less.

The reaction pressure does not have an appreciable effect on the reaction; thus atmospheric pressure is preferred, but subatmospheric and superatmospheric pressures can be used.

For step (c), it is not necessary to remove the product of step (b) from the reaction vessel. Workup of the step (b) product is not required; the step (b) product can be used as formed. In step (c), the $NaAlR'_4$ product produced in step (b) is reacted with a trihalosilane. Thus, a reactant employed in the process of step (c) is an alkyltrihalosilane, $RSiX_3$. In this reactant, R is a lower alkyl radical such as methyl, ethyl, propyl, butyl, isopropyl, sec-butyl, or the like. Preferably, R is unbranched. More preferably, R is methyl. The three groups indicated by X are halide radicals; preferably all three are the same; however, reactants with two or three halo groups per molecule can be used. More preferably, the halide groups are chloro or bromo radicals, most preferably they are all chloro groups.

Although not bound by any theory, it is believed the process of step (c) of this invention can be represented by the following equation:

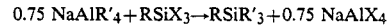
$$0.75\ NaAlR'_4 + RSiX_3 \rightarrow RSiR'_3 + 0.75\ NaAlX_4$$

In step (c) the ratio of metal aluminate to trihaloalkylsilane employed is preferably from about 0.75 to about 1.0 to 1.0.

In an alkali metal aluminum tetraalkyl ($MAlR'_4$) used in step (c), all the organic radicals need not be the same. Thus as taught above, a reactant with dissimilar groups can be formed from a mixture of olefins (such as a mixture of octene-1 and decene-1). Alternatively, one may use a mixture of two or more metal aluminates wherein each one is prepared from a single olefin. Hence for example in this invention, one can use a mixture of two or more separately produced aluminates, such as $NaAl(C_8H_{17})_4$ and $NaAl(C_{10}H_{21})_4$.

The ability to use a mixture of aluminates is important, since a mixture can be chosen to produce a silane product with desired physical properties.

In many instances where a mixture of alkyl groups occurs within the metal aluminate starting material, the products obtained by the process of step (c) are substantially in the calculated, statistical ratios. For example, reaction of $CH_3SiCl_3$ with $NaAl(C_8H_{17})_2(C_{10}H_{21})_2$ can yield a mixture of products, $CH_3Si(C_8H_{17})_3$, $CH_3Si(C_8H_{17})_2(C_{10}H_{21})$, $CH_3Si(C_8H_{17})(C_{10}H_{21})_2$, and $CH_3Si(C_{10}H_{21})_3$ in a relative mole quantity that approximates 0.125, 0.375, 0.375, 0.125, as predicted for random distribution.

The process of step (c) is conducted using a temperature that is high enough to cause the reaction to take place at a reasonable rate, but not so high that it causes an undesirable amount of side reaction or decomposition to occur. Generally speaking, a temperature about 150° C. and below 230° C. is used. Preferably, the temperature is from about 180° C. to 200° C.

The reaction time is not a truly independent variable but depends at least to some extent on the other reaction conditions employed, such as the reaction temperature.

Generally speaking, reaction is essentially complete in from about 3 to 10 hours with 5 to 6 hours being typical.

The reaction pressure does not have a large effect on the course of step (c). Atmospheric, subatmospheric and superatmospheric pressure can be used. Atmospheric pressure or the autogenous pressure of the system are preferred.

Thus in a preferred embodiment step (c) can be defined as a process for the preparation of a tetraalkylsilane having the formula:

$$R-\underset{\underset{R'}{|}}{\overset{\overset{R'}{|}}{Si}}-R'$$

wherein R and R' are alkyl radicals and the radicals R' are alike or different, such that R has up to about 4 carbon atoms, and each radical designated by R' has from about 8 to about 14 carbon atoms; said process comprising contacting reactants (i) and (ii) wherein:

(i) is an alkali metal aluminum tetraalkyl having the formula MAlR'$_4$, wherein M is lithium, sodium, or potassium, and R' has the same significance as above, and (ii) is an alkyltrihalosilane having the formula RSiX$_3$, wherein X is a halide radical selected from fluoride, chloride and bromide, and R has the same significance as above; said process being conducted such that the mole ratio of reactant (a) to reactant (b) is from about 0.75 to 1.0, to about 1 to 1, and the reaction temperature is from about 180° C. to about 230° C. For step (c) product workup can be conducted as follows.

Optionally, sodium aluminum hydride is added (to reduce any unreacted CH$_3$SiCl$_3$ to CH$_3$SiH$_3$) and the resultant mixture stirred for about 3 hours at room temperature. In this step, any CH$_3$SiH$_3$ formed is evolved as a gas.

The mixture is then hydrolyzed with 3N HCl. The organic phase (which contains the product) is separated and dried. The products of this invention may contain, in addition to the desired tetraalkyl silane, some olefin dimer and/or some RSiR'$_2$H by-product.

The above-described product workup can be conducted by two related, alternative procedures. As described above, the entire reaction product can be utilized in the workup. This method is convenient for small scale, laboratory preparations. Alternatively, before product workup the NaAlCl$_4$ (or analogous co-product) can be separated from the organic layer. In this alternative method, the workup procedure is conducted on the organic fraction after separation of the inorganic co-product. Preferably, the inorganic co-product is removed as a liquid while it is in a molten state. Generally speaking, the process of this invention is conducted above the melting point of NaAlCl$_4$ co-product; and therefore, the co-product can be discharged in a molten state from the reaction vessel, and then separated from the remainder of the product mixture. This is the preferred procedure for larger scale preparations.

The treatment of the reaction mixture with sodium aluminum hydride is utilized to facilitate analysis of the product mixture. Therefore, it does not comprise an essential part of the process, and it is not necessary to include this step in the workup of the reaction mixture.

EXAMPLE 1

To a one liter pressure vessel was added:

| | | |
|---|---|---|
| 7.7 ml | Al(C$_2$H$_5$)$_3$ | (0.056 mole) |
| 19.1 g | sodium | (0.830 mole) |
| 22.3 g | aluminum | (0.826 mole) |
| 625 ml | octene-1 | (3.99 mole) |

The aluminum contained 1900 ppm titanium.

The mixture was heated at 140° C. under hydrogen pressure of 2000 psig. Heating was continued for four hours. After that time, the reaction rate was slowing, but reaction was not yet complete.

The reactor was cooled and vented. The viscous black product was diluted with heptane and filtered to remove solids. The filtrate weighed 551 g.

Analysis indicated that 3.21% of Al was present, and 2.73 mmoles of gas per gram was liberated on hydrolysis. These results indicate that the product roughly corresponds to NaAlR'$_2$R"$_2$, wherein R' is octyl and R" is H and ethyl. The yield was 76.1%.

The material was charged back to the reactor, and heated an additional three hours at 170° C. Analysis showed the product contained 3.6 wt. % Al, and 1.45 mmoles of gas per gram was liberated on hydrolysis; thus the product corresponds to NaAlR'$_{2.92}$Et$_{0.13}$H$_{0.96}$ wherein R' is octyl, and Et is ethyl.

The remaining material was charged back to the reactor, 40 mmoles of tri-n-octyl aluminum (TNOA) was added, and the resultant mixture heated for 3 hours at 170–175° C. Analysis indicated the product corresponded to NaAlR'$_{3.9}$R"$_{0.10}$ wherein R' is octyl, and R" is ethyl and hydrogen.

EXAMPLE 2

To a one liter pressure vessel was charged:
0.375 m trioctylaluminum (TNOA),
0.556 m sodium,
0.581 m aluminum, and
400 ml of a mixture 1.65/1.0 of octene-1 and decene-1.

The mixture was reacted with H$_2$ at 140° C. and 2000 psig for 3.5 hours.

The reactor was cooled and vented; and additional olefin to bring the total to four moles, and an additional 0.05 moles of TNOA was added. The resultant mixture was reacted at 170–175° C. for 3 hours under 2000 psig H$_2$.

A product sample showed less than 1 weight % aluminum in soluble form. Thus it appears that TNOA is a poor catalyst for NaAlH$_4$ conversion, i.e. formation of NaAlH$_4$ under the reaction conditions employed.

EXAMPLE 3

To the reactor was charged:
0.02 mole of triethylaluminum (TEA),
0.43 mole Na,
0.456 mole Al,
230.7 g octene-1, and
159.6 g decene-1.

The resultant reaction mixture was heated at 140° C. and 2000 psig hydrogen for 4.5 hours. Reaction was sluggish.

After cooling and venting the reactor, 0.01 mole of additional TEA was added. This brought the total catalyst concentration to 7.5 mole % based on sodium.

During repressuring with $H_2$, blow through on the hydrogen feed line was noted, indicating $H_2$ consumption may have been better than originally thought. The reaction mixture was reacted an additional 3.5 hours at 140° C. and 2000 psig.

The reaction mixture was cooled and vented and 0.04 mole of TNOA added. The resultant mixture was reacted further for 3 hours at 170–175° C. Sampling of the reactor indicated 415.2 g of product having 2.74% aluminum, and 0.16 mmole of gas/gram was liberated on hydrolysis. This corresponds to a product $NaAlR_{3.85}R''_{0.15}$, and a yield of 84.1%. In the product formula, R=octyl and decyl and R''=hydrogen and ethyl.

EXAMPLE 4

The following was charged to a one liter pressure vessel:
0.6675 mole Na,
0.697 mole Al,
0.045 mole TEA,
274 g octene-1, and
190 g decene-1.
The resultant mixture was reacted for six hours at 2000 psig and at 140° C.

The vessel was cooled and vented, and 0.06 mole of TNOA was added. The resultant mixture was reacted for a further three hour period at 170°–175° C. After cooling, the product was sampled and analyzed. It contained 3.66 weight percent aluminum, and 0.21 mmoles of gas per gram on hydrolysis. The gas was 50.3 mole percent ethane and 49.7 mole % hydrogen. This corresponds to an aluminate product having the formula $NaAlR'_{3.85}H_{0.07}R''_{0.08}$, wherein R' is a mixture of octyl and decyl and R'' is ethyl and hydrogen.

The product weighed 504.3 g and contained 0.683 moles of aluminate. After correcting for catalysts charged, the yield was calculated to be 92.5%.

EXAMPLE 5

To a reactor was charged:
283 g of aluminate product of Example 4,
250 ml of heptane, and
0.451 mole $CH_3SiCl_3$.
The aluminum/silicon ratio in the mixture was 0.85. The resultant mixture was reacted by heating for 5 hours at 190° C.

The cooled reaction vessel was hydrolyzed with dilute HCl as taught above then washed with water, and then vacuum stripped to yield a silahydrocarbon product having the following composition as shown by gas liquid chromatography.

| Compound | Mole Fraction |
|---|---|
| MeSi(Oct)$_3$ | 0.28 |
| MeSi (Oct)$_2$ (Dec) | 0.41 |
| MeSi (Oct) (Dec)$_2$ | 0.21 |
| MeSi (Oct)$_2$ C$_{16}$ | 0.011 |
| MeSi (Dec)$_3$ | 0.042 |
| MeSi (Oct) (Dec)C$_{16}$ | 0.024 |
| MeSi (Oct) (Dec)C$_{18}$ | 0.016 |
| MeSi (Oct) (Dec)C$_{20}$ | 0.004 |

In the above formulas, "Me"=methyl, "Oct"=octyl, "Dec"=decyl, $C_{16}$=hexyldecyl, $C_{18}$=octadecyl, and $C_{20}$=eicosyl.

The material was purified by passage through a basic alumina column to yield a product having an acid number below 0.05 mg KOH/g.

Viscosity measurements were made and shown to be within the U.S. Air Force specification for silahydrocarbon base stock.

| Temperature | Viscosity in Centistokes | |
|---|---|---|
| | Product | Air Force Specification |
| −54° C. | 2380 | <2500 |
| 38° C. | 9.79 | 9.5 min. |
| 100° C. | 2.70 | 2.3 min. |

The above results indicate that products made by the process of this invention are useful as functional fluids. Thus, products of this invention are useful as hydraulic fluids for military or other applications. Hydraulic fluids are used in hydraulic systems to transmit pressure or energy. They also serve to reduce friction in bearings, and between sliding surfaces in pumps and similar articles. Hydraulic and other functional fluids also protect surfaces from rusting, and can remove undesirable particulate matter away from surfaces.

Like other functional fluid base stocks, the silahydrocarbons produced by the process of this invention can be admixed with additives such a rust inhibitors, antiwear agents, corrosion inhibitors and the like.

The process of this Example can be extended to the use of sodium, lithium and potassium aluminum tetraalkyls in which the alkyl groups are octyl, decyl, dodecyl or tetradecyl. Such substances may be reacted with methyl, ethyl, n-propyl, isopropyl, or n-butyl trichlorosilane or the trifluoro or tribromo analogs of these substances. The reaction can be conducted at exogenous pressure or at pressures of up to 500 psi or higher, imposed by use of an inert gas atmosphere, e.g. nitrogen or argon. The reactions can be conducted at 180° C. to 230° C. for 3 to 10 hours. The mole ratio of metal aluminate to trihalosilane is in the range of about (0.75–1.0) to 1.0.

Although not bound by any theory, from the results of the above examples it appears that the above illustrated preferred embodiments of this invention involve a first step in which $NaAlH_4$ is formed (from Na, Al and $H_2$ in the presence of an organoaluminum catalyst). The $NaAlH_4$ is then transformed to a $NaAlR'_4$ product in a second step that is also catalyzed by an organoaluminum catalyst. In a third step, the aluminate product is reacted to form a silahydrocarbon as illustrated by equation (1) above.

In the first step, effectiveness of the catalyst decreases with increasing size of R''' in R'''$_3$Al. This is illustrated by Example 2. Also in the first step, the catalyst appears to be converted to one or more species inoperative in the second step. This might take place according to the process illustrated by the following two equations.

$$4Al(C_2H_5)_3 + 3Na \rightarrow 3NaAl(C_2H_5)_4 \qquad \ldots (2)$$

$$3NaAl(C_2H_5)_4 + 3Na + 2\,Al \rightarrow 6NaAl(C_2H_5)_2H_2 \qquad \ldots (3)$$

Since the catalyst is apparently effectively destroyed by such a process, the substitution of the fourth hydrogen in $NaAlH_4$ by an alkyl group is essentially uncatalyzed, and therefore very slow. In general, while the aluminates shown in Equations (2) and (3) are useful catalysts in the synthesis of sodium aluminum hydride step (a), they are not effective catalysts for the addition of olefin to $NaAlH_4$, step (b). In step (b), fresh catalyst is added to speed up the reaction. The utility of $AlR_3$ catalysts in step (b) suggests that lithium catalysts may also be used in that step.

It is to be understood that modification of the above described invention can be made without departing from the spirit and scope of the following claims.

I claim:

1. Process for the preparation of a compound having the formula $RSiR'_3$ wherein R and R' are alkyl radicals and the R' radicals are alike or different, such that R has up to about 4 carbon atoms, and each R' has from about 8 to about 14 carbon atoms, said process comprising:
   (a) reacting sodium, aluminum and a straight chain alpha olefin having from about 8 to about 14 carbon atoms in the presence of hydrogen under pressure and a catalytic quantity of an organoaluminum compound, and at a reaction temperature of from about 130° C. to about 180° C.;
   (b) adding additional organoaluminum catalyst to the product of step (a) and reacting the resultant mixture thereby produced at a temperature of from about 130° C. to about 80° C.;
   (c) mixing an $RSiX_3$ reactant with the reaction product of step (b), the radical R in said reactant having the same significance as above, and the radical X being a halogen radical such that each X is alike or different; and reacting the thereby produced reaction mixture at a temperature of from about 180° C. to about 230° C. to form product having said formula $RSiR'_3$.

2. The process of claim 1 wherein the reaction products of step (a) and (b) are not isolated prior to subsequent reaction.

3. The process of claim 1 wherein all three alkyl groups represented by R' are the same.

4. The process of claim 3 wherein the R' groups are $C_8$ and $C_{10}$ alkyl radicals.

5. The process of claim 4 wherein said reactant $RSiX_3$ is methyltrichlorosilane.

6. The process of claim 5 wherein said hydrogen pressure is from about 1500 to about 2500 psig.

7. The process of claim 3 wherein said organoaluminum catalyst in step (b) has the formula $R'_3Al$ and each radical R' corresponds to R' in $RSiX_3$.

8. The process of claim 7 wherein the amount of organoaluminum catalyst in step (b) does not exceed about 7 mole percent.

9. The process of claim 8 wherein the amount of organoaluminum catalyst added in step (a) is about 7 mole percent.

10. The process of claim 1 wherein step (a) is catalyzed by triethylaluminum.

* * * * *

UNITED STATES PATENT AND TRADEMARK OFFICE
CERTIFICATE OF CORRECTION

PATENT NO. : 4,845,260

DATED : July 4, 1989

INVENTOR(S) : Gunner E. Nelson

It is certified that error appears in the above-identified patent and that said Letters Patent is hereby corrected as shown below:

Column 9, line 25, reads "80°C.;" and should read -- 180°C.; --.

Signed and Sealed this

Fifth Day of June, 1990

*Attest:*

HARRY F. MANBECK, JR.

*Attesting Officer*      *Commissioner of Patents and Trademarks*